United States Patent [19]

Bryan et al.

[11] Patent Number: 4,990,452

[45] Date of Patent: Feb. 5, 1991

[54] COMBINING MUTATIONS FOR STABILIZATION OF SUBTILISIN

[75] Inventors: Philip N. Bryan, Silver Spring; Michael W. Pantoliano, Germantown, both of Md.

[73] Assignee: Genex Corporation, Gaithersburg, Md.

[21] Appl. No.: 180,756

[22] Filed: Apr. 12, 1988

Related U.S. Application Data

[63] Continuation-in-part of Ser. No. 180,757, Apr. 12, 1988, which is a continuation-in-part of Ser. No. 34,964, Apr. 6, 1987, and a continuation-in-part of Ser. No. 34,965, Apr. 6, 1987, each is a continuation-in-part of Ser. No. 828,545, Feb. 12, 1986, abandoned.

[51] Int. Cl.[5] .......................... C12N 15/00; C12N 9/34; C12N 9/54; C12N 9/56

[52] U.S. Cl. .................................. 435/222; 435/172.3; 435/221; 252/174.12; 935/10; 935/14; 935/29

[58] Field of Search .................... 435/172.3, 69.1, 188, 435/235, 320, 222, 221, 91, 172.1; 935/14, 10, 29; 252/547, 174.12

[56] References Cited

U.S. PATENT DOCUMENTS 4,760,025 7/1988 Estell .................................. 435/222

OTHER PUBLICATIONS

Cunningham, B. C., et al., 1987, Protein Engineering 1(4) 319–329.

Nedkov P. et al., 1985 (Apnl.), Biol. Chem. Hoppe–Seyler, 336:421–430.

Estell, D. A. et al., *J. Biol. Chem.*, 260: 6518–6521 (1985).

Liao, H. et al., *Proc. Natl. Acad. Sci USA* 83:576–580 (1986).

Estell, D. A. et al., *World Biotech. Rep.* 2:181–187 (1984).

Pantoliano, M. W. et al., *Biochemistry* 26:2077–2082 (1987).

Bryan, P. N. et al., *Proteins: Structure, Function & Genetics*, 1:326–334 (1986).

Bryan, P. et al., *Proc. Natl. Acad. Sci. USA* 83:3743–3745 (1986).

Vasantha, N. et al., *Genet. Biotechnol. Bacilli* 2:163–172 (1983).

Wells, J. A. et al., *Genet. Biotechnol. Bacilli* 2:173–180 (1983).

Shortle, D. et al., *Proc. Natl. Acad. Sci. USA* 75: 2170–2174 (1978).

Vasantha, N. et al., *J. Bacteriol.* 159: 811–819 (1984).

Jacobs, M. et al., *Nucl. Acids Res.* 13: 8913–8926 (1985).

Kurihara, M. et al., *J. Biol. Chem.* 247: 5619–5631 (1972).

Svendsen, I. et al., *FEBS Letts.* 196: 228–232 (1986).

Meloun, B. et al., *FEBS Lett.* 183: 195–200 (1985).

Jany, K. D. et al., *Biol. Chem. Hoppe-Seyler* 366: 485–492 (1985).

McPhalen, C. A. et al., *FEBS Lett.* 188: 55–58 (1985).

Pahler, A. et al., *EMBO J.* 3: 1311–1314 (1984).

Myers, R. M. et al., *Science* 229: 242–247 (1985).

Folk, W. R. et al., *Cell* 33: 585–593 (1983).

Wells, J. A. et al., *Nucl. Acids Res.* 11: 7911–7925 (1983).

*Primary Examiner*—Robin L. Teskin
*Assistant Examiner*—Michelle S. Marks
*Attorney, Agent, or Firm*—Saidman, Sterne, Kessler & Goldstein

[57] ABSTRACT

The invention relates to modified subtilisin enzymes which have increased thermal stability. The modified subtilisin enzymes have at least two or more amino acid mutations which confer increased thermal stability. It has been discovered that combining individual stabilizing mutations in subtilisin frequently results in an additive increase in thermal stability. In addition, the invention pertains to cloned mutant genes coding for a subtilisin material having at least two amino acid substitution which has increased thermal stability.

2 Claims, 2 Drawing Sheets

COMBINING MUTATIONS FOR STABILIZATION OF SUBTILISIN

CROSS-REFERENCE TO RELATED APPLICATIONS

This application is a continuation-in-part application of pending U.S. Ser. No. 07/180,757, filed Apr. 12, 1988, which is a continuation-in-part of pending U.S. Ser. No. 07/034,964, filed Apr. 6, 1987, and which is also a continuation-in-part of pending U.S. Ser. No. 07/034,965, filed Apr. 6, 1987, both applications being continuation-in-part applications of U.S. Ser. No. 06/828,545, filed Feb. 12, 1986, now abandoned, the contents of each are fully incorporated herein by reference.

FIELD OF THE INVENTION

The invention pertains to modified subtilisin enzymes which have enhanced thermal stability and to the genes which encode the subtilisin enzymes.

BACKGROUND OF THE INVENTION

Proteins are linear polymers of amino acids. Since the polymerization reactions which produce proteins result in the loss of one molecule of water from each amino acid, proteins are often said to be composed of amino acid "residues." Natural protein molecules may contain as many as 20 different types of amino acid residues, each of which contains a distinctive side chain. The sequence of amino acids in a protein defines the primary structure of the protein.

Proteins fold into a three-dimensional structure. The folding is determined by the sequence of amino acids and by the protein's environment. The remarkable properties of proteins depend directly from the protein's three-dimensional conformation. Thus, this conformation determines the activity or stability of enzymes, the capacity and specificity of binding proteins, and the structural attributes of receptor molecules.

The three-dimensional structure of a protein may be determined in a number of ways. Perhaps the best known way of determining protein structure involves the use of the technique of X-ray crystallography. An excellent general review of this technique can be found in *Physical Biochemistry,* Van Holde, K. E. (Prentice-Hall, N.J. (1971) pp221–239) which reference is herein incorporated by reference. Using this technique, it is possible to elucidate three-dimensional structure with remarkable precision. It is also possible to probe the three-dimensional structure of a protein using circular dichroism, light scattering, or by measuring the absorption and emission of radiant energy (Van Holde, *Physical Biochemistry,* Prentice-Hall, N.J. (1971)). Additionally, protein structure may be determined through the use of the techniques of neutron defraction, or by nuclear magnetic resonance (*Physical Chemistry,* 4th Ed. Moore, W. J., Prentice-Hall, N.J. (1972) which reference is hereby incorporated by reference).

The examination of the three-dimensional structure of numerous natural proteins has revealed a number of recurring patterns. Alpha helices, parallel beta sheets, and anti-parallel beta sheets are the most common patterns observed. An excellent description of such protein patterns is provided by Dickerson, R. E., *et al.* In: *The Structure and Action of Proteins,* W. A. Benjamin, Inc., Calif. (1969). The assignment of each amino acid to one of these patterns defines the secondary structure of the protein. The helices, sheets and turns of a protein's secondary structure pack together to produce the three-dimensional structure of the protein. The three-dimensional structure of many proteins may be characterized as having internal surfaces (directed away from the aqueous environment in which the protein is normally found) and external surfaces (which are in close proximity to the aqueous environment). Through the study of many natural proteins, researchers have discovered that hydrophobic residues (such as tryptophan, phenylalanine, tyrosine, leucine, isoleucine, valine, or methionine) are most frequently found on the internal surface of protein molecules. In contrast, hydrophilic residues (such as aspartic acid, asparagine, glutamate, glutamine, lysine, arginine, histidine, serine, threonine, glycine, and proline) are most frequently found on the external protein surface. The amino acids alanine, glycine, serine and threonine are encountered with equal frequency on both the internal and external protein surfaces.

Proteins exist in a dynamic equilibrium between a folded, ordered state and an unfolded, disordered state. This equilibrium in part reflects the short range interactions between the different segments of the polypeptide chain which tend to stabilize the protein's structure, and, on the other hand, those thermodynamic forces which tend to promote the randomization of the molecule.

The largest class of naturally occurring proteins is made up of enzymes. Each enzyme generally catalyzes a different kind of chemical reaction, and is usually highly specific in its function. Enzymes have been studied to determine correlations between the three-dimensional structure of the enzyme and its activity or stability.

The amino acid sequence of an enzyme determines the characteristics of the enzyme, and the enzyme's amino acid sequence is specified by the nucleotide sequence of a gene coding for the enzyme. A change of the amino acid sequence of an enzyme may alter the enzyme's properties to varying degrees, or may even inactivate the enzyme, depending on the location, nature and/or magnitude of the change in the amino acid sequence.

Although there may be slight variations in a distinct type of naturally occurring enzyme within a given species of organism, enzymes of a specific type produced by organisms of the same species generally are substantially identical with respect to substrate specificity, thermal stability, activity levels under various conditions (e.g., temperature and pH), oxidation stability, and the like. Such characteristics of a naturally occurring or "wild-type" enzyme are not necessarily optimized for utilization outside of the natural environment of the enzyme. It may thus be desirable to alter a natural characteristic of an enzyme to optimize a certain property of the enzyme for a specific use, or for use in a specific environment.

SUMMARY OF THE INVENTION

The invention relates to modified subtilisin enzymes which have increased thermal stability. The modified subtilisin enzymes have at least two or more amino acid mutations which confer increased thermal stability. It has been discovered that combining individual stabilizing mutations in subtilisin frequently results in an additive increase in thermal stability. In addition, the invention pertains to cloned mutant genes coding for a subtilisin material having at least two amino acid substitution conferring increased thermal stability.

DEFINITIONS

Figure 1:
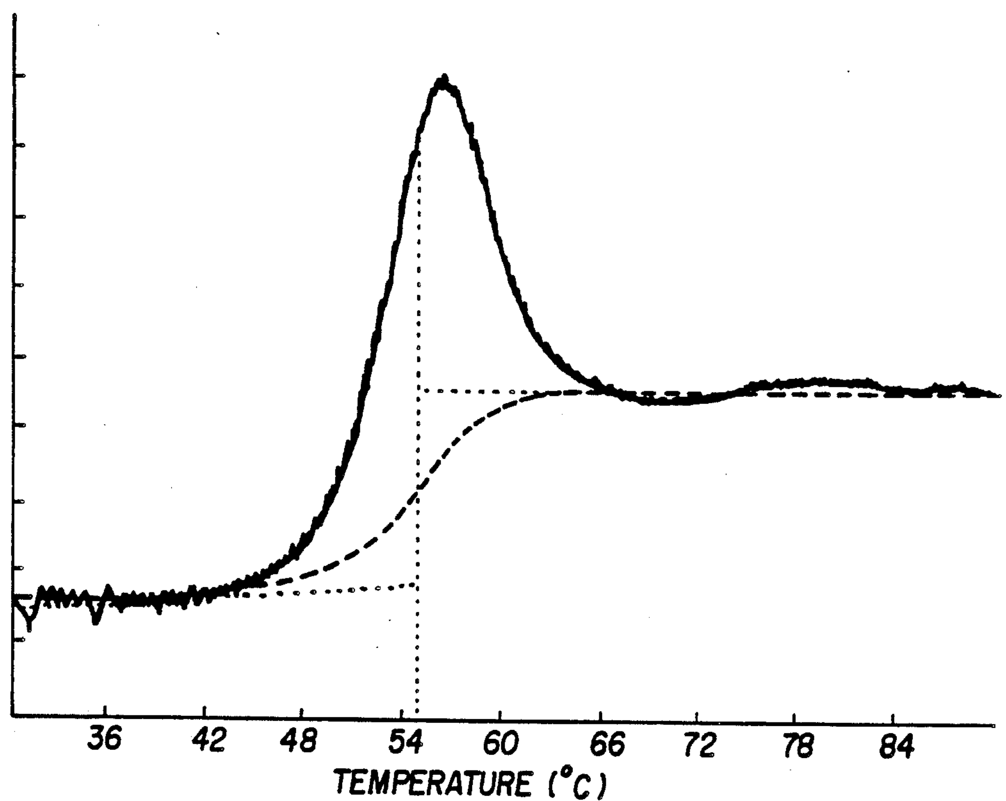
FIG. 1 depicts a graph of the melting profile of wild-type subtilisin in 10 mM EDTA, pH 8.0.

The following definitions are used in describing the invention.

PROTEIN

A protein is a heteropolymer made by living cells and composed of amino acids. A typical protein comprises 100 to 1000 amino acids. The exact sequence of amino acids determines the structure and function of the protein.

AMINO ACID

Amino acids are naturally occurring compounds that are the building blocks of proteins. The natural amino acids are usually abbreviated to either three letters or one letter. The most common amino acids, and their symbols, are given in Table 1. The amino acids are joined head to tail to form a long main chain. Each kind of amino acid has a different side group.

TABLE 1

Amino acid names and abbreviations.

| Amino Acid | Three letter code | Single letter code |
|---|---|---|
| Alanine | Ala | A |
| Arginine | Arg | R |
| Aspartic acid | Asp | D |
| Asparagine | Asn | N |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophane | Trp | W |
| Tyrosine | Tyr | Y |
| Valine | Val | V |

ATOM NAMES

All amino acids have the same atoms in the main chain and differ only in the side chains. The main-chain atoms are a nitrogen, two carbons, and one oxygen. The first atom is the nitrogen, called N. The next atom is a carbon and is called the alpha-carbon. Side groups are attached to this alpha-carbon. The alpha-carbon is connected to the carbonyl carbon which is called C. C is connected to the carbonyl oxygen (called O) and to the N of the next residue. The side group atoms are given names composed of the symbol for the element (C, O, N, S), a Greek letter (alpha, beta, gamma, delta, epsilon, zeta and eta), and perhaps an arabic numeral if the side group is forked.

DETAILED DESCRIPTION OF THE INVENTION

This invention pertains to subtilisin enzymes that have been modified by mutating the various nucleotide sequences that code for the enzymes. The modified subtilisin enzymes of this invention have enhanced thermal stability.

The subtilisin enzymes of this invention belong to a class of enzymes known as proteases. A protease is a catalyst for the cleavage of peptide bonds. An example of this cleavage is given below.

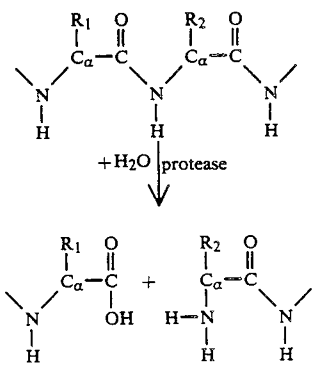

One type of protease is a serine protease. A serine protease will catalyze the hydrolysis of peptide bonds in which there is an essential serine residue at the active site. Serine proteases can be inhibited by phenylmethanesulfonylfluoride and by diisopropylfluorophosphate.

A subtilisin is a serine protease produced by Gram positive bacteria or by fungi. The amino acid sequences of seven subtilisins are known. These include five subtilisins from Bacillus strains (subtilisin BPN', subtilisin Carlsberg, subtilisin DY, subtilisin amylosacchariticus, and mesenticopeptidase). (Vasantha *et al.*, "Gene for alkaline protease and neutral protease from *Bacillus amyloliquefaciens* contain a large open-reading frame between the regions coding for signal sequence and mature protein," J. Bacteriol. 159:811-819 (1984); Jacobs *et al.*, "Cloning sequencing and expression of subtilisin Carlsberg from *Bacillus licheniformis,*" *Nucleic Acids Res.* 13:8913-8926 (1985); Nedkov *et al.*, "Determination of the complete amino acid sequence of subtilisin DY and its comparison with the primary structures of the subtilisin BPN', Carlsberg and amylosacchariticus," *Biol. Chem. Hoppe-Seyler* 366:421-430 (1985); Kurihara *et al.*, "Subtilisin amylosacchariticus," *J. Biol. Chem.* 247:5619-5631 (1972); and Svendsen *et al.*, "Complete amino acid sequence of alkaline mesentericopeptidase," *FEBS Lett.* 196:228-232 (1986)).

The amino acid sequence of the subtilisin thermitase from *Thermoactinomyces vulgaris* is also known. (Meloun *et al.*, "Complete primary structure of thermitase from *thermoactinomyces vulgaris* and its structural features related to the subtilisin-type proteases," *FEBS Lett.* 183:195-200 (1985).)

The amino acid sequences from two fungal proteases are known: proteinase K from *Tritirachium album* (Jany *et al.*, "Proteinase K from Tritirachium albam Limber," *Biol. Chem. Hoppe-Seyler* 366:485-492 (1985)) and thermomycolase from the thermophilic fungus, *Malbranchea pulchella* (Gaucher *et al.*, "Endopeptidases: Thermomycolin," *Methods Enzymol,* 45:415-433 (1976)).

These enzymes have been shown to be related to subtilisin BPN', not only through their primary sequences and enzymological properties, but also by comparison of x-ray crystallographic data. (McPhalen *et al.*, "Crystal and molecular structure of the inhibitor eglin from leeches in complex with subtilisin Carlsberg," *FEBS Lett.* 188:55–58 (1985) and Pahler *et al.*, "Three-dimensional structure of fungal proteinase K reveals similarity to bacterial subtilisin," *EMBO J.* 3:1311–1314 (1984).)

As used in this invention, the term "mutated or modified subtilisin enzyme(s)" is meant to include mutated serine proteases that have enhanced thermal stability: and are homologous to the subtilisin enzymes of this invention. The mutated or modified subtilisin enzymes are also described herein as "subtilisin material." As used herein, and under the definition of mutated or modified subtilisin enzyme or subtilisin material, the mutations of this invention may be introduced into any serine protease which has at least 50%, and preferably 80% amino acid sequence homology with the sequences referenced above for subtilisin BPN', subtilisin Carlsberg, subtilisin DY, subtilisin amylosacchariticus, mesenticopeptidase, thermitase, proteinase K, or thermomycolase, and therefore may be considered homologous.

The mutated subtilisin enzymes of this invention have enhanced thermal stability over native or wild-type subtilisin. Thermal stability is a good indicator of the overall robustness of a protein. Proteins of high thermal stability often are stable in the presence of chaotropic agents, detergents, and under other conditions, which tend to inactivate proteins. Thermally stable proteins are therefore expected to be useful for many industrial and therapeutic applications, in which resistance to high temperature, harsh solvent conditions or extended shelf-life is required.

Further, it has been discovered that combining individual stabilizing mutations in subtilisin frequently results in approximately additive increases in the free energy of stabilization. Thermodynamic stability was also shown to be related to resistance to irreversible inactivation at high temperature and high pH. The single-site changes of this invention individually do not exceed a 1.5 Kcal/mol contribution to the free energy of folding. These small incremental increases in the free energy of stabilization, however, result in dramatic increases in overall stability when mutations are result in dramatic increases in overall stability when mutations are combined, since the total free energy of folding for most proteins is in the range of 5–15 kcals/mol (Creighton, T. E., in *Proteins: Structure and Molecular Properties,* W. H. Freeman and Company, New York (1984)).

X-ray crystallographic analysis of several combination mutants reveals that conformation changes associated with each mutation tend to be highly localized with minimal distortion of the backbone structure. Thus, very large increases in stability can be achieved with no radical changes in the tertiary protein structure but, rather, minor independent alterations in amino acid sequence. As previously suggested (Holmes, M. A., and Matthews, B. W., *J. Mol. Biol.* 160:623 (1982)), contributions to the free energy of stabilization can be gained in many different ways, including improved hydrogen bonding and hydrophobic interactions in the folded form and decreased chain entropy of the unfolded enzyme.

Thermostable enzymes generally will have extended half-lives at all temperatures, thereby improving bioreactor and shelf-life performance. This demonstration that subtilisin BPN' can be converted into a thermophilic enzyme without sacrificing catalytic properties indicates that the stability of many proteins can be radically improved through this same step-by-step process.

The individual amino acid mutations detailed in Table 2 have been found to be thermally stabilizing mutations. Thus, the mutated subtilisin enzymes of this invention have at least two of these specific amino acid position substitution that enhances thermal stability. In Table 2, the naturally occuring amino acid and position number is given first with the arrow to the right indicating the amino acid substitution. The mutations were made using subtilisin BPN'. However, as explained herein, these mutations can be introduced at analogous positions in other serine proteases using oligonucleotidedirected mutagenesis.

TABLE 2

| | Mutations in subtilisin BPN' |
|---|---|
| 1 | Val8→Ile |
| 2 | Thr22→Cys, Ser87→Cys |
| 3 | Thr22→Lys, Asn76→Asp |
| 4 | Met50→Phe |
| 5 | Ser53→Thr |
| 6 | Ser63→Asp, Tyr217→Lys |
| 7 | Asn76→Asp |
| 8 | Ser78→Asp |
| 9 | Tyr104→Val, Gly128→Ser |
| 10 | Ala116→Glu |
| 11 | Leu126→Ile |
| 12 | Gly131→Asp |
| 13 | Gly166→Ser |
| 14 | Gly169→Ala |
| 15 | Pro172→Asp |
| 16 | Pro172→Glu |
| 17 | Ser188→Pro |
| 18 | Gln206→Cys |
| 19 | Gln206→Tyr |
| 20 | Ala216→Cys, Gln206→Cys |
| 21 | Tyr217→Lys |
| 22 | Tyr217→Leu |
| 23 | Asn218→Asp |
| 24 | Gln206→Tyr |
| 25 | Ser248→Asp, Ser249→Arg |
| 26 | Thr254→Ala |
| 27 | Gln271→Glu |

Resistance to thermal inactivation is measured by resistance to thermal inactivation under two representative sets of conditions. The first is in the presence of 10 mM calcium chloride at 65° C. and the second is at 45° C. in the presence of 10 mM EDTA, which removes free calcium from solution. Calcium is known to stabilize subtilisin. Measurements of stability under these two extremes of calcium concentration were made because potential commercial uses of stable subtilisins could involve conditions with varying amounts of calcium present. The T1/2 of wild-type BPN' subtilisin is 59 ±3 minutes in 10 mM CaCl at 65° C. and 14.4 ±0.05 minutes in 1 mM EDTA at 45° C. The thermal stability of the mutated subtilisin is expressed as a ratio of T1/2 (mutant) divided by the T1/2 (wild-type).

Table 3 shows the strain designation of the host cell secreting the mutated subtilisin enzymes and compares their half-lives relative to wild type.

TABLE 3

Mutated Subtilisin BPN' Enzymes.

| Strain | Mutation | T½ compared to wild type enzyme 10 mM CaCl | 1.0 mM EDTA |
|---|---|---|---|
| GX7130 | Wild Type | 1.0 | 1.0 |
| GX7174 | VAL8→ILE | 2.0 | 0.8 |
| GX7175 | GLY169→ALA | 5.9 | 1.1 |
| GX7181 | ASN218→ASP | 5.2 | 4.0 |
| | THR22→CYS | | |
| | SER87→CYS | | |
| GX7186 | ASN218→SER | 29 | 5.3 |
| | THR22→CYS | | |
| | SER87→CYS | | |
| | GLY169→ALA | | |
| GX7195 | TYR217→LYS | 3.3 | 2.7 |
| GX7199 | THR22→CYS | 10 | |
| | SER87→CYS | | |
| | GLY169→ALA | | |
| | PRO172→ASP | | |
| GX8303 | MET50→PHE | 0.76 | 1.4 |
| GX8309 | SER248→ASP | 1.5 | 0.75 |
| | SER249→ARG | | |
| GX8314 | GLN206→CYS | 2.4 | 5.1 |
| GX8321 | THR22→CYS | — | 36 |
| | SER87→CYS | | |
| | GLY169→ALA | | |
| | MET50→PHE | | |
| | TYR217→LYS | | |
| | ASN218→SER | | |
| GX8324 | THR22→CYS | — | 168 |
| | SER87→CYS | | |
| | GLY169→ALA | | |
| | MET50→PHE | | |
| | TYR217→LYS | | |
| | ASN218→SER | | |
| | GLN206→CYS | | |
| GX8330 | TYR217→LEU | 2.0 | 1.8 |
| GX8336 | GLN206→TYR | 1.1 | 1.7 |
| GX8350 | MET5→PHE | 400 | |
| | GLY169→ALA | | |
| | GLN206→CYS | | |
| | TYR217→LYS | | |
| | ASN218→SER | | |
| | ASN76→ASP | | |
| GX8352 | SER63→ASP | 6.3 | — |
| | TYR217→LYS | | |
| GX8354 | GLN271→GLU | 1.3 | — |
| GX8363 | THR22→LYS | 1.3 | 2.1 |
| | ASN76→ASP | | |
| GX8372 | MET50→PHE | — | 630 |
| | GLY169→ALA | | |
| | GLN206→CYS | | |
| | TYR217→LYS | | |
| | ASN76→ASP | | |
| | SER78→ASP | | |
| | ASN218→SER | | |
| GX8376 | TYR104→VAL | 5.0 | 1.6 |
| | GLY128→SER | | |
| GX7148 | GLY131→ASP | 1.5 | 0.9 |
| GX7150 | ASN218→SER | 3.5 | 2.6 |
| GX7164 | ASN218→ASP | 1.9 | 1.5 |
| GX7178 | SER188→PRO | 1.8 | — |
| GX7188 | ALA116→GLU | 1.3 | 1.05 |
| GX7189 | LEU126→ILE | 1.4 | 1.1 |
| GX8301 | ASN218→SER | 7.4 | — |
| | GLY166→SER | | |
| GX8305 | SER53→THR | 2.0 | — |
| GX8306 | ASN218→SER | 7.0 | — |
| | THR254→ALA | | |
| GX8315 | ASN218→SER | 11.4 | — |
| | GLY131→ASP | | |
| | THR254→ALA | | |
| GX7159 | THR22→CYS | 1.05 | 1.5 |
| | SER87→CYS | | |
| GX8307 | GLN206→CYS | | |
| | SER87→CYS | | |
| | GLN206→CYS | | |
| | GLN206→CYS | | |
| | ALA216→CYS | | |
| GX7172 | PRO172→ASP | 1.5 | 1.1 |
| GX8312 | PRO172→GLU | 2.0 | 1.0 |
| GX8347 | ASN76→ASP | — | 2.5 |
| GX8364 | SER78→ASP | — | 1.5 |
| GX8373 | ASN218→ASP | — | 400 |
| | MET50→PHE | | |
| | GLY169→ALA | | |
| | GLN206→CYS | | |
| | TYR217→LYS | | |
| | ASN76→ASP | | |
| | SER78→ASP | | |

Using the information of the subtilisin enzyme mutations of Tables 2 and 3, one can improve other proteases which are closely related, subtilisin Carlsberg for example. Closeness of relation is measured by comparison of amino acid sequences. There are many methods of aligning protein sequences, but the differences are only manifest when the degree of relatedness is quite small. The methods described in *Atlas of Protein Sequence and Structure,* Margaret O. Dayhoff editor, Vol. 5 Supplement 2, 1976, National Biomedical Research Foundation, Georgetown University Medical Center, Washington, D.C., p. 3 ff., entitled SEARCH and ALIGN, define relatedness. As is well known in the art, related proteins can differ in number of amino acids as well as identity of each amino acid along the chain. That is, there can be deletions or insertions when two structures are aligned for maximum identity. For example, subtilisin Carlsberg has only 274 amino acids, while subtilisin BPN' has 275 amino acids. Aligning the two sequences shows that Carlsberg has no residue corresponding to ASN56 of subtilisin BPN'. Thus the amino acid sequence of Carlsberg would appear very different from BPN' unless a gap is recorded at location 56. Therefore, one can predict with high degree of confidence that, for example, substituting SER for ASN at location 218 of subtilisin Carlsberg will increase thermal stability, provided that the residues in Carlsberg are numbered by homology to BPN'.

When one of the two homologous subtilisins has a gap, one must infer that the structures are different at that position. Examples of such differences are well known in the art. Because of these local differences, one should not transfer stabilizing mutations if either subtilisin has a gap at, or immediately adjacent, to the site of the mutation. Therefore, after aligning the amino acid sequences, those mutations at or next to gaps are deleted from the list of desirable mutations and the mutation is not made.

One can use this reasoning to transfer all of the themostable mutations described herein to other homologous serine proteases.

In brief, in order to introduce the enhanced themostable mutation(s) of this invention, the gene coding for the desired subtilisin material generally is first isolated from its natural source and cloned in a cloning vector. Alternatively, mRNA which is transcribed from the gene of interest can be isolated from the source cell and converted into cDNA by reverse transcription for insertion into a cloning vector. A cloning vector can be a phage or plasmid, and generally includes a replicon for autonomous replication of the vector in a microorganism independent of the genome of the microorganism. A cloning vector advantageously includes one or more phenotypic markers, such as DNA coding for antibiotic resistance, to aid in selection of microorganisms transformed by the vector.

Procedures for insertion of DNA or cDNA into a vector for cloning purposes are well known in the art. These procedures generally include insertion of the gene coding for the subtilisin material into an opened restriction endonuclease site in the vector, and may involve addition of homopolymeric tails of deoxynucleotides to the ends of the gene and linking the gene to opened ends of a cloning vector having complementary homopolymeric tails. A subtilisin gene can then be mutated by oligonucleotide-directed mutagenesis. Oligonucleotidedirected mutagenesis, also called site-directed mutagenesis, is described in detail in Bryan *et al., Proc. Natl. Acad. Sci. U.S.A.* 83:3743–3745 (1986), incorporated herein by reference.

The mutant subtilisin material of this invention can be used as an additive to washing preparations, such as detergents, which are used for cleaning, in particular for cleaning clothes. The mutant subtilisin material of this invention is more thermally stable than wild-type subtilisin material and thus does not lose activity as rapidly as wild-type when stored in solution with detergents or when subjected to high heat during use in cleaning. By use of the mutant subtilisin material of this invention as an additive in washing preparations, the removal of proteinaceous stains on fabric is improved. The amount of mutant subtilisin material that may be used as an additive to washing preparations are well known in the art, or may readily be ascertained by routine experimentation. The optimal range of enzyme concentration will, of course, be related to the cost of the enzyme and the amount of cleaning needed. Typically, the amount of mutated subtilisin material added to a washing preparation will be from about 2000 to about 4000 Alkaline Delft Units/gram (ADU/gm) of washing preparation.

The invention is illustrated by the following examples which are not intended to be limiting.

EXAMPLES

Example I

Thermostability Studies

The ability to engineer more stable proteins should broaden their utility for many industrial and therapeutic purposes. Because most proteins are probably not optimized for stability over the course of evolution, the engineering of substantial increases in stability often may be achievable with relatively minor modifications in a starting structure. Experimental results thus far appear consistent with this idea. More stable versions of several proteins including subtilisin {(Bryan *et al., Proteins: Structure, Function and Genetics* 1:326 (1986); Pantoliano *et al., Biochem.* 26:2077 (1987); and Cunningham, B. C., and Wells, J. A., *Protein Engineering* 1:319 (1987)), T4 (Matthews *et al., Proc. Natl. Acad. Sci. U.S.A.* 84:6663 (1987); Perry, L. J., and Wetzel, R., *Science* 226:555 (1984)), staphylococcal nuclease (Shortle, D., and Lin, B., *Genetics* 110:539 (1985)), dihydrofolate reductase (Villafranca *et al., Science* 222:782 (1983)), lambda repressor (Hecht *et al., Proteins: Structure, Function and Genetics* 1:43 (1986)), and kanamycin nucleotidyltransferase (Liao *et al., Nature* 323:356 (1986)) have been described. Recent crystallographic studies have shown in general that only subtle and highly localized structural differences distinguish a stability mutant from the parent protein (Bryan *et al.* (1986), *supra;* Matthews *et al.* (1897), *supra;* and Alber *et al., Nature* 330:41 (1987)). Furthermore, random mutagenesis experiments indicate that stabilizing mutational events are fairly common. On the order of one percent of the amino acid changes produced by chemical mutagens in subtilisin increase the free energy of unfolding by 0.5 Kcals/mol or more.

Though stabilizing mutations appear to be prevalent, the design of stabilizing modifications in a protein structure remains a hit or miss affair. In fact, the most successful design approaches so far have not been based on a precise knowledge of the effects of a specific amino acid change on the folded structure, but rather its inferred effects on the unfolded form. For example, the configurational entropy of the unfolded form of a protein and thereby the entropy of unfolding can be decreased by replacing glycine residues substituting in proline residues, or introducing disulfide crosslinks (Pantoliano *et al.* (1987), *supra;* Matthews *et al.* (1987), *supra;* Hecht *et al.* (1986), *supra*}.

Even though the effects of a given mutation on the free energy of the folded state cannot be predicted with precision, we demonstrate here that engineering large increases in stability are possible nonetheless. We present here several independently isolated variants of subtilisin BPN'; each significantly increases the free energy of unfolding and resistance to irreversible thermal inactivation. Combining these individual stabilizing mutations results, for example, in a variant melting 15.7 degrees higher and with a half-time of thermal inactivation, 200 times longer than the wild-type subtilisin BPN' at high temperature or high pH. Calorimetric data demonstrate that independent, incremental increases in the free energy of stabilization resulting from combining individual stabilizing mutations results in approximately additive increases in overall stability. We therefore have been able to increase stability in subtilisin in a step-by-step fashion. Stabilizing mutations have been designed or identified by random mutagenesis and screening and then combined to produce a subtilisin with stability increases accrued from each of the individual changes.

The subtilisin gene from *Bacillus amyloliquefaciens* (subtilisin BPN') has been cloned and sequenced previously and expressed at high levels from its natural promoter sequences in *Bacillus subtilis* (Vasantha *et al., Bacteriol,* 159:881 (1984); Wells *et al., Nucleic Acids Res.* 11:7911 (1983)). This has enabled us to introduce mutations *in vitro* into the plasmid-encoded subtilisin gene and conveniently analyze their effect on the thermostability of the altered enzyme. All mutant genes were recloned into a pUB110-based expression plasmid (Bryan *et al., Proteins: Structure, Function and Genetics* 1:326 (1986)) and used to transform *B. subtilis.* The *B. subtilis* strain used as the host contains a chromosomal deletion of its subtilisin gene and therefore produces no background wild-type activity. All mutant enzymes were efficiently expressed from this vector and were secreted into the culture medium at a concentration of about 1 g/l. Subtilisin is the major secreted protein in this system and comprises almost 80% of the total extracellular protein. Wild-type subtilisin and the variant enzymes were purified essentially as described in Bryan *et al., Proc. Nat'l. Acad. Sci. U.S.A.* 83:3743 (1986).

CALORIMETRY

The relative thermodynamic stabilities of mutant and wild-type enzymes were determined using differential scanning calorimetry (DSC). The amount of excess heat absorbed by a protein sample as the temperature is increased through a transition from the folded to unfolded state at constant pressure provided a direct measurement of the enthalpy of unfolding (Privalov and Potekhin, *Methods in Enzymology* 131:4 (1986); Takahashi and Sturtevant, *Biochemistry* 20:6185 (1981)). With subtilisin, however, the autolysis that accompanies the unfolding process complicates this analysis. In the studies reported here, this problem was circumvented to some extent by addition of the competitive inhibitor, N-dansyl-3-aminobenzeneboronic acid, which has Ki=2μM at pH 8.0 (Philip and Marupuri, *FEBS Lett.* 133:36 (1981)). However, the small amount of autolytic activity that remains prevents an accurate determination of a calorimetric ΔH. Nevertheless, under the conditions we have used the rate of thermal unfolding appears to be rapid in relation to the rate at which autolysis and/or aggregation remove unfolded molecules from the equilibrium of the native and denatured states. Therefore, the midpoint for the thermal unfolding transition, Tm, accurately reflects the temperature at which the concentration of folded and unfolded states is approximately equal (i.e., ΔG=0). The increases in Tm resulting from the stabilizing mutations can thus be used to calculate the increases in ΔG of the unfolding reaction.

The melting profile of wild-type subtilisin in 10 mM EDTA, pH 8.0, is shown in FIG. 1. We have chosen to report results obtained in the presence of EDTA for the following reasons. Subtilisin BPN' is greatly stabilized when its two calcium binding sites are occupied. By using EDTA to remove free calcium from solution, the effects of mutations on the intrinsic stability of the enzyme can be measured, as opposed to their effects on calcium binding affinity. Secondly, because the major industrial use of subtilisin is as an additive to laundry detergents, which contain metal chelating agents, stability measurements under conditions of low free calcium concentrations are relevant to this application.

Using a computer program for DSC analysis, the subtilisin melting profiles were compared to various models for unfolding. The data for wild-type (FIG. 1) fit very closely to a two-state model. On the basis of the two-state model, a temperature corrected v'ant Hoff ΔH was calculated. For three independent melting experiments, the calculated δH was 94,100±5000 cal/mol. Using the midpoint of the melting transition for the temperature at which ΔG=0(54.8±0.2°), ΔS is calculated to be 286 cal/deg mol.

The melting temperatures and associated free energy changes of all single and combination mutants are summarized in Table 4. Comparison of the free energy of unfolding of individual mutants with that of combination mutants shows that the free energy changes associated with each individual change generally accrue in an approximately additive manner when they are combined into the same molecule.

TABLE 4

| Strain | Mutations | ΔTm | Kcal/mol ΔΔG | ΔΔG (sum) |
|---|---|---|---|---|
| Wild-type BPN' | — | — | — | — |
| 7150 | N218S | 4.9° | 1.4 | — |
| 7159 | T22C,S87C | 2.6° | 0.7 | — |
| 7175 | G169A | 1.6° | 0.4 | — |
| 8303 | M50F | 2.3° | 0.6 | |
| 7195 | Y217K | 3.4° | 0.9 | |
| 8314 | Q206Cox | 5.4° | 1.5 | |
| 7181 | N218S<br>T22CS87C | 7.7° | 2.1 | 2.1 |
| 7186 | N218S<br>T22C,S87C<br>G169A | 9.2° | 2.6 | 2.5 |
| 8316 | N218S<br>T22C,S87C<br>G169A<br>M50F | 10.4° | 2.9 | 3.2 |
| 8321 | N218S<br>T22C,S87C<br>G169A<br>M50F<br>Y217K | 12.5° | 3.5 | 3.8 |
| 8324 | N218S<br>T22C,S87C<br>G169A<br>M50F<br>Y217K<br>Q206Cox | 15.7° | 4.4 | 5.0 |

*Calculated from the relationship ΔTm = ΔΔGmut-wild type/ΔS (Becktel, W. J. and Schellman, J. A., Biopolymers 26:1859 (1987)).

KINETICS OF IRREVERSIBLE INACTIVATION

We have also tried to examine possible correlations between thermodynamic stability and resistance to irreversible inactivation under two very different sets of conditions. The kinetics of inactivation for wild-type and mutant strain 8324 have been measured both at 57° C., pH 8.0 (A), and at 25° C., pH 12.0 (B) (FIG. 2).

The precise mechanism of irreversible thermal inactivation of a protease is complicated, possibly involving unfolding, aggregation, autolysis and other components. Under the conditions used here, however, the rate of thermal inactivation of wild-type and variant 8324 obeys first-order kinetics over four half-lives, indicating that the rate-determining step in the process is unimolecular.

Figure 2A:
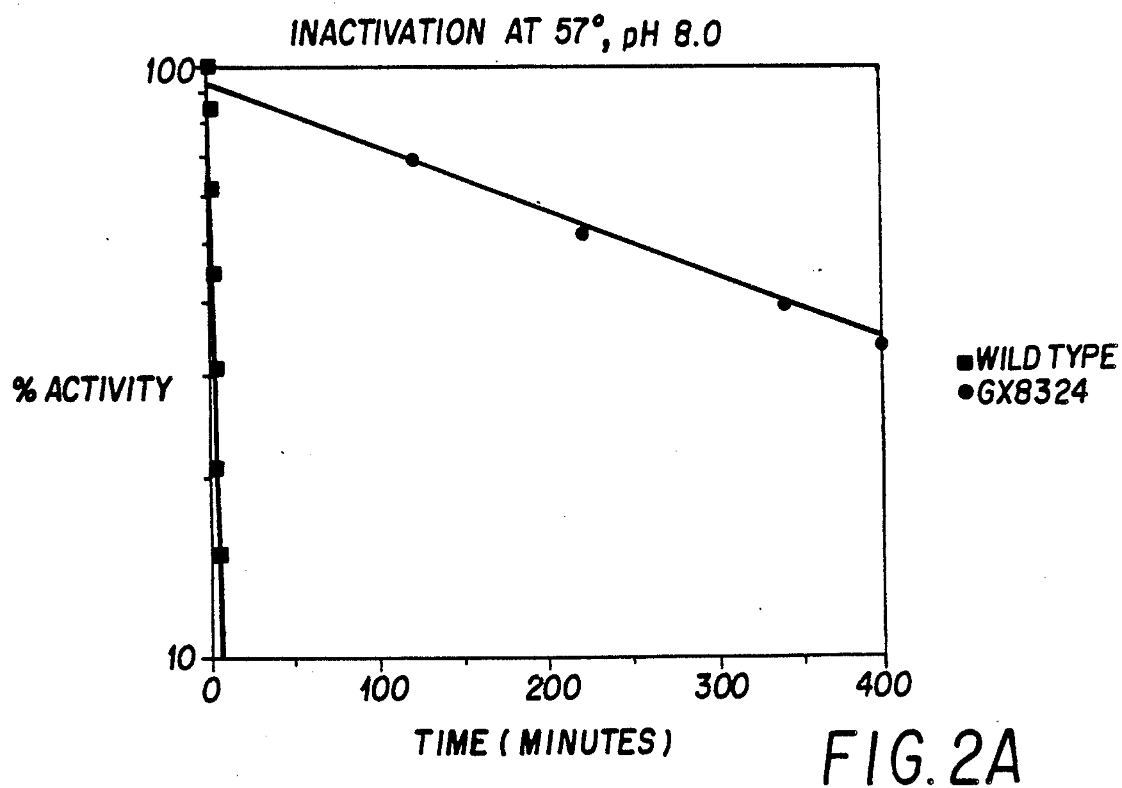
FIG. 2A and 2B depict graphs of the kinetics of inactivation for wild-type and mutant strain 8324 measured at 57° C., pH 8.0 (A) and at 25° C., pH 12.0 (B).
Figure 2B:
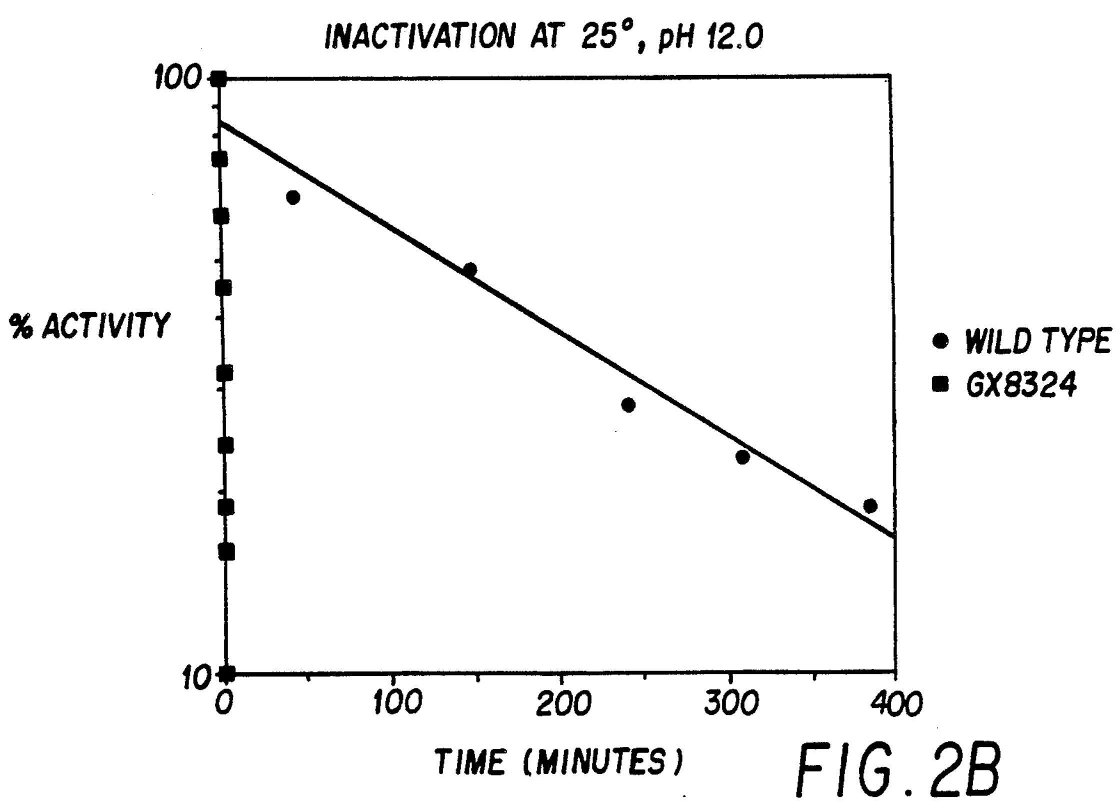

The 8324 combination variant is inactivated 200 times slower than wild-type both at 57°, pH 8.0, and at 25°, pH 12.0 (FIG. 2). Resistance to irreversible inactivation at high pH and high temperature appears to be correlated to increased thermodynamic stability. This suggests that the highest energy barrier in the inactivation process of wild-type and 8324 under conditions of high temperature and high pH is related to an unfolding event.

X-RAY CRYSTAL STRUCTURES

In order to analyze the structural relationships among the six stabilizing modifications, six high-resolution crystal structures were compared. Crystals were grown by vapor diffusion against 55% acetone in hanging drops (Bryan *et al., supra*), and large single crystals of wild-type and mutant subtilisins were obtained within two to seven days. The crystals were isomorphous with the monoclinic crystal form reported by Drenth and Hol (Drenth and Hol, *J. Mol. Biol.* 28:543 (1967)), belonging to space group P21 with cell dimensions a=41.6Å, b=79.5Å, c=37.3Å, and d=114.5Å.

Diffraction intensities were measured with a Xentronics imaging proportional counter mounted on a modified Supper oscillation camera utilizing an Elliott GX-21 x-ray source. Single crystals were used to collect each data set to 1.8Å resolution.

Initial models were determined by Fourier difference analysis and then subjected to extensive crystallographic refinement by using restrained least-squares procedures. All non-hydrogen protein atoms, 184 ordered water molecules, two acetone molecules, and two calcium atoms were included in the refinement. A detailed structural comparison of the N218S variant (7150) and wild-type has been previously reported. The structures of these two enzymes were found to be superimposible to 0.07Å for C positions and 0.10 for all atoms. The only region deviated from these values by more than two-fold was in the immediate vicinity of residue 218. Next the structure of 22-87C,S218 variant (7181) was determined and found by these same criteria to differ from the 7150 variant only in the vicinity of the substituted residues, 22 and 87. The same was found to be true when the structures of variants 7186, 8321, and 8324 were determined and compared.

These mutations contribute to the free energy of stabilization in a variety of ways including improved hydrogen bonding and hydrophobic interactions in the folded form and decreased chain entropy of the unfolded enzyme. The comparisons reported here demonstrate that on a structural level the effects of these mutations are independent and highly localized at least as far as can be determined by the 1.8Å x-ray crystal structures. Because of the subtlety of the structural changes associated with each of these modifications, the basic structure of even the highly altered and stable variant such as 8324 is still very similar to wild-type.

ACTIVITY

Subtilisin activity was assayed by monitoring the hydrolysis of 0.1 mM solutions of peptide substrate, succinyl-(L)-Ala-(L)-Ala-(L)-Pro-(L)-Phe-p-nitroanilide (SAAPF-pNA) at 25° C. as described by Delmar *et al.* (*Anal. Biochem.* 99:316 (1979)). Kinetic parameters are shown in Table 5. Most of the mutations result in improvements in catalytic parameters against SAAPF. Relative proteinase activity against azocasein, however, is as low as 50% of that of wild-type. Most of the loss of proteinase activity can be attributed to the S218 mutation, which by itself is 25% less active than wild-type (Table 5). Clearly, stabilizing mutations do not necessarily affect catalytic activity adversely, even though enzymes from thermophilic organisms are generally not as active at 25° as their mesophilic counterparts (Brock, *Science* 230:132 (1985)). Thermophilic enzymes are likely not constrained in evolution to be highly efficient catalysts because of the high temperature at which their reactions are carried out. Since we were selective in combining only stabilizing mutations which individually have relatively minor effects on proteinase activity, the activity of several of the combined variants remains similar to that of wild-type.

TABLE 5

| | SAAPF-pNA | | Relative Proteinase Activity |
|---|---|---|---|
| Mutant | Km (μM) | kcat (sec$^{-1}$) | (azocasein) |
| Wild type | 172 ± 2 | 46.8 ± 0.2 | 1.00 |
| N218S | 115 ± 4 | 61 ± 4 | 0.75 ± 0.02 |
| T22C,S87C | 209 ± 17 | 47 ± 3 | 0.95 ± 0.03 |
| G169A | 86 ± 9 | 60 ± 3 | 0.93 ± 0.02 |
| M50F | 94 ± 2 | 44 ± 2 | 0.97 ± 0.02 |
| Y217K | 99 ± 4 | 59 ± 3 | 1.18 ± 0.04 |
| Q206Cox | | | 0.99 ± 0.05 |

TABLE 5-continued

| | SAAPF-pNA | | Relative Proteinase Activity |
|---|---|---|---|
| Mutant | Km (μM) | kcat (sec$^{-1}$) | (azocasein) |
| 7181 | | | 0.73 ± 0.02 |
| 7186 | 64 ± 1 | 64 ± 3 | 0.68 ± 0.01 |
| 8316 | | | 0.54 ± 0.04 |
| 8321 | 173 | 150 | 0.72 ± 0.06 |
| 8324 | | | 0.75 ± 0.05 |

CONCLUSION

We have found that combining individual stabilizing mutations in subtilisin can result in approximately additive increases in the free energy of stabilization. Thermodynamic stability was also shown to be related to resistance to irreversible inactivation at high temperature and high pH. Thermodynamic analysis has shown that each modification individually contributes between (0.4–1.5 kcal/mol) to the free energy of stabilization. In fact, of more than 20 stabilizing single-site changes that have been isolated, none exceeds a 1.5 Kcal/mol contribution to the free energy of folding. The total free energy of folding for most proteins is in the range of 5–15 kcals/mol (Creighton, T. E., in *Proteins: Structure and Molecular Properties,* W. H. Freeman and Company, New York (1984)). However, these small incremental increases in the free energy of stabilization result in dramatic increases in overall stability when mutations are combined. The 8324 variant is 4.4 Kcal/mol more stable than wild-type subtilisin BPN'.

X-ray crystallographic analysis of several combination mutants reveals that conformation changes associated with each mutation tend to be highly localized with minimal distortion of the backbone structure. Thus, very large increases in stability can be achieved with no radical changes in the tertiary protein structure but, rather, minor independent alterations in amino acid sequence. As previously suggested (Holmes, M. A., and Matthews, B. W., *J. Mol. Biol.* 160:623 (1982)), contributions to the free energy of stabilization can be gained in many different ways including improved hydrogen bonding and hydrophobic interactions in the folded form and decreased chain entropy of the unfolded enzyme.

The 8324 mutant has a melting temperature 15.7° higher than wild-type and has a half-life 200 times longer both at high temperature and high pH. Thermostable enzymes generally will have extended half-lives at all temperatures, thereby improving bio-reactor and shelf-life performance. This demonstration that subtilisin BPN' can be converted into a thermophilic enzyme without sacrificing catalytic properties indicates that the stability of many proteins can be radically improved through this same step-by-step process which we have pursued.

EXAMPLE II

More than 20 variants have been isolated with increased resistance to thermal inactivation (Table 6). Among these stable variants, the half-time of thermal inactivation of subtilisin is increased between 1.3-fold and 5-fold by an individual mutation. It has been found, however, that stabilizing mutations generally can be combined to produce variants with stability accrued from each of the individual mutations. Thus, extremely stable variants can be constructed in a step by step manner. Combining independently isolated stabilizing mutations generally has resulted in an approximate multiplicative increase in the half-time of thermal inactivation (Table 6).

For example, in one construction the 22–87 disulfide mutations (GX7159) were combined in the ASN218-SER mutation (GX7150) to create variant GX7181. The ASN218-SER mutation by itself increases the T1/2 of thermal inactivation 2.6-fold over wild type and the 22–87 disulfide by 1.5-fold. The double mutant exhibits approximately the combined stability of both individual changes and has a T1/2 of thermal inactivation 4.0 times that of wild type.

Six additional examples of this principle are listed in Table 6.

X-ray crystallographic and thermodynamic analysis of several of these mutants have shown that subtle and highly localized changes in structure can result in significant increases in stability. Analysis of the stabilizing mutants by differential scanning calorimetry has shown none to contribute more than 1.5 kcal/mol to the free energy of folding. This amount of stabilization is significant because the total free energy of unfolding for most proteins is in the range of 5–15 kcals/mol. Therefore, the small incremental increases in the free energy of stabilization resulting from combining individual stabilizing mutations results in dramatic increases in overall stability. These increases in stability can be achieved with no radical changes in the tertiary protein structure but rather minor, independent alterations in amino acid sequence.

Combining stabilizing mutations should be a general method for obtaining large increases in stability in most proteins. These findings have some important commercial implications because thermostable enzymes generally will have extended half-lives at all temperatures and solvent conditions thereby improving bioreactor and shelf-life performance.

TABLE 6

Examples of Combinations of Independently Discovered Stabilizing Mutations

| Strain | Mutation | T½ compared to wild type enzyme: 10 mM CaCl | 1.0 mM EDTA |
|---|---|---|---|
| GX7130 | Wild Type | 1.0 | 1.0 |
| GX7181 | ASN218→ASP | 5.2 | 4.0 |
| | THR22→CYS | | |
| | SER87→CYS | | |
| GX7186 | ASN218→SER | 29 | 5.3 |
| | THR22→CYS | | |
| | SER87→CYS | | |
| | GLY169→ALA | | |
| GX7199 | THR22→CYS | 10 | — |
| | SER87→CYS | | |
| | GLY169→ALA | | |
| | PRO172→ASP | | |
| GX8321 | THR22→CYS | — | 36 |
| | SER87→CYS | | |
| | GLY169→ALA | | |
| | MET50→PHE | | |
| | TYR217→LYS | | |
| | ASN218→SER | | |
| GX8324 | THR22→CYS | — | 168 |
| | SER87→CYS | | |
| | GLY169→ALA | | |
| | MET50→PHE | | |
| | TYR217→LYS | | |
| | ASN218→SER | | |
| | GLN206→CYS | | |
| GX8350 | MET50→PHE | — | 400 |
| | GLY169→ALA | | |
| | GLN206→CYS | | |
| | TYR217→LYS | | |
| | ASN218→SER | | |
| | ASN76→ASP | | |
| GX8372 | MET50→PHE | — | 630 |
| | GLY169→ALA | | |
| | GLN206→CYS | | |
| | TYR217→LYS | | |
| | ASN218→SER | | |
| | ASN76→ASP | | |
| | SER78→ASP | | |
| GX8373 | ASN218→ASP | — | 400 |
| | MET50→PHE | | |
| | GLY169→ALA | | |
| | GLN206→CYS | | |
| | TYR217→LYS | | |
| | ASN76→ASP | | |
| | SER78→ASP | | |

Although the foregoing invention has been described by way of illustration and example for purposes of clarity and understanding, it will be obvious that certain changes and modifications may be practiced within the scope of the invention, as limited only the scope of the appended claims.

What is claimed is:

1. A thermally stable subtilisin coded for by a mutant BPN' gene comprising the following amino acid substitutions:

phenylalamine at amino acid position 50;
alanine at amino acid position 169;
cysteine at amino acid position 206;
lysine at amino acid position 217;
serine at amino acid position 218; and
asparagine at amino acid position 76.

2. A washing preparation comprising the subtilisin of claim 1.

* * * * *

UNITED STATES PATENT AND TRADEMARK OFFICE
CERTIFICATE OF CORRECTION

PATENT NO. : 4,990,452

DATED : February 5, 1991

INVENTOR(S) : Bryan et al

It is certified that error appears in the above-identified patent and that said Letters Patent is hereby corrected as shown below:

Column 16, line 57, "asparagine at amino acid position 76" should read --aspartic acid at amino acid position 76.--

Signed and Sealed this

Eighteenth Day of August, 1992

*Attest:*

DOUGLAS B. COMER

*Attesting Officer*

*Acting Commissioner of Patents and Trademarks*